United States Patent [19]

Akiyama et al.

[11] Patent Number: 5,087,793
[45] Date of Patent: Feb. 11, 1992

[54] PROCESS FOR PREPARING INNER OLEFINES

[76] Inventors: Naoki Akiyama; Masaharu Mori, both of c/o Mitsubishi Monsanto Chemical Company Yokkaichi-Kenkyusho: 1, Toho-cho, Yokkaichi-shi, Mie-ken, Japan

[21] Appl. No.: 476,433

[22] Filed: May 24, 1990

[30] Foreign Application Priority Data

Sep. 27, 1988 [JP] Japan ................................. 63-242168

[51] Int. Cl.$^5$ ................................................. C07C 5/23
[52] U.S. Cl. ...................................... 585/666; 585/664
[58] Field of Search ................................. 585/666, 664

[56] References Cited

U.S. PATENT DOCUMENTS

| | | | |
|---|---|---|---|
| 3,409,699 | 11/1968 | Mitsche | 585/666 |
| 3,428,704 | 2/1969 | Fishel | 585/666 |
| 3,751,502 | 8/1973 | Hayes et al. | 585/666 |
| 4,749,819 | 6/1988 | Hamilton, Jr. | 585/666 |

*Primary Examiner*—Anthony Mc Farlane
*Assistant Examiner*—Nhat Phan

[57] ABSTRACT

Inner olefines are prepared by using 1-olefines having 6 to 34 carbon atoms as a starting material and isomerizing them at temperatures ranging from 130° to 270° C. in the presence of mordenite type zeolites. Optionally, unreacted 1-olefines can be separated and reused as a starting material.

5 Claims, No Drawings

PROCESS FOR PREPARING INNER OLEFINES

TECHNICAL FIELD

The present invention relates to a process for preparing inner olefines (olefines having their double bonds in the inner side of their molecular chain) by using 1-olefines as starting materials and isomerizing them. Specifically, the present invention relates to a process for preparing inner olefines to be used as starting materials for preparing alkenyl succinic anhydrides which are useful as sizing agents in the paper industry, by using 1-olefines as starting materials.

BACKGROUND ART

As catalysts to be present in the reaction system that 1-olefines as starting materials are isomerized to inner olefines having their double bond in the inner side of their molecular chains, there has been known acids and bases (metals), specifically inorganic acids such as sulfuric acid, phosphoric acids, etc., alcoholates, sodium, potassium and the like (Yuki-gosei-Kagaku, 874, 30 (1972)).

However, when inorganic acids are used, a large amount of polymers of 1-olefines are formed as by-products and the control of isomerization reaction is difficult. On the other hand, metal catalysts or catalysts bearing metals on carriers having a large surface area such as alumina, silica gel, activated carbon, etc. (e.g. Journal of American Chemical Society, 82, 382 (1969)) have high catalytic activities, but they can cause firing by exposure to air or absorb moisture to become inactivated, therefore being inconvenient in handling.

Japanese Patent Kokai Publication No. 62-39582 describes using solid acid-base catalysts including silica/alumina/iron types and silica/titania types as isomerization catalysts. Japanese Patent Kokai Publication No. 63-135596 describes using mordenite as an isomerization catalyst. However, the former tends to form self-polymers of 1-olefines at a high rate and further, both of the former and the latter exhibit a low reactivity of 1-olefines, therefore being left the problem that they can not increase the overall yield.

The inventors performed various investigations to dissolve the above problems involved in the preparation of inner olefines having their double bonds in the inner sides of their molecular chains by isomerization of 1-olefines as starting materials, and have eventually found out that the use of mordenite-type zeolites as a catalyst to be present in the isomerization reaction system and the control of reaction conditions to a specific state can inhibit self-polymerization of 1-olefines to thereby obtain isomerized inner olefines at a high yield and additionally that the above process is excellent in catalyst stability, thus accomplishing the present invention.

SUMMARY OF THE INVENTION

The present invention is a process for preparing inner olefines comprising using 1-olefines having 6 to 34 carbon atoms as a starting material and conducting isomerization reaction in the presence of mordenite type zeolites at temperatures ranging from 130° C. to 270° C.

DETAILED DESCRIPTION OF THE INVENTION

The present invention is described below. 1-olefines to be used in the present invention are individual olefines of 6 to 34 carbon atoms represented by the general formula

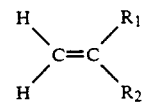

wherein $R_1$ is hydrogen or an alkyl group of 1 to 4 carbon atoms, $R_2$ is an alkyl group having a linear or branched chain, and the total carbon number of $R_1$ and $R_2$ is 4 to 32, preferably 8 to 22, or mixtures of these olefines.

Specific examples of these olefines include the following ones which may be used solely or as a mixture.

Linear 1-olefines:
Octene-1, nonene-1, decene-1, undecene-1, dodecene-1, tridecene-1, tetradecene-1, pentadecene-1, hexadecene-1, heptadecene-1, octadecene-1, nonadecene-1, eicosene-1, etc.

1-Olefines having a branched chain:
4-Methyl-1-octene, 5-propyl-1-octene, 5-ethyl-1-dodecene, 7-propyl-1-decene, 8-ethyl-1-decene, 5-ethyl-1-dodecene, 6-propyl-1-tridecene, 11-ethyl-1-tetradecene, 10-propyl-1-eicosene, 16-ethyl-1-tricosene, etc.

In the present process, mordenite-type zeolites are used as an isomerization catalyst. These zeolites are used in the hydrogen form or as partially or wholly changed to the metal form. The metal is not limited to a specific kind, but preferred particularly are sodium, iron, manganese, magnesium, nickel, etc.

To isomerize 1-olefines according to the present invention, the above catalysts can be usually present in the reaction system at an amount of 0.05% by weight or more, preferably 0.1 to 10% by weight, more preferably 0.3 to 10% by weight based on 1-olefines. Also, reaction temperature can be controlled within a range of 130° C. to 270° C., preferably 130° to 250° C., more preferably 150° to 250° C.

When the amount of catalyst is below the above range, the yield of isomerization is low, while when it exceeds the above range, the yield of isomerization no more increases, therefore being disadvantageous from the viewpoint of cost. On the other hand, when the isomerization reaction temperature is below 130° C., the yield of isomerization is low, while when it exceeds 270° C., formation of self-polymers of 1-olefines is promoted and the yield of isomerized inner olefines is decreased, therefore not preferable.

Reaction pressure during isomerization of 1-olefines to inner olefines can be ambient, increased or decreased, but 5 kg/cm2 if pressurized and 10 mmHg or higher if evacuated are preferred, respectively.

Procedure of isomerization of 1-olefines to inner olefines according to the present invention generally comprises adding mordenite-type zeolites as aforementioned to 1-olefines as a starting material, then mixing them to be uniform, and heating the reaction system for 0.5 to 6 hours at temperatures ranging from 130° to 270° C. in the atmosphere of nitrogen gas with stirring. Samples are taken from the reaction mixture in mid course, and the doule bond distribution of formed inner olefines is monitored during the isomerization reaction by using e.g. ozone-triphenylphosphine reduction chromatography. After completion of isomerization reaction, the catalyst added to the reaction system is filtered away to obtain the desired inner olefines.

According to the process of the present invention, double bond distribution of inner olefines can be controlled to some extent by adequately selecting the reaction temperature condition upon isomerization of starting 1-olefines. For example, when temperatures of 130° to 180° C. are selected, inner olefines having their double bonds at positions 2 and 3 can be predominantly formed. On the contrary, when temperatures of higher than 180° C. are selected, inner olefine mixture having their double bonds widely distributed over the whole molecular chains can be formed.

In the mean time, addition of catalyst at smaller amounts may improve the selectivity to positions 2 and 3, but in those cases, unreacted 1-olefines may be left at a higher level under certain conditions. However, it is possible to separate 1-olefines from inner olefines by fractional distillation and accordingly, the overall yield of the process can be improved by separating 1-olefines and recirculating them to use as a starting material.

As described above, the present invention is to have mordenite type zeolites be present in the reaction system and isomerize 1-olefines to inner olefines under specific conditions. The present invention has the following advantages, thus highly useful in the industry:

(1) The amount of self-polymer of starting 1-olefines formed during preparation of inner olefines is small and the yield of isomerized inner olefines is high.

(2) It is excellent in catalyst stability. For example, as compared to sodium metal catalyst used in the prior art, the risk of firing or the decrease in activity due to moisture absorption is suppressed and the handling of catalyst is easier.

(3) The position and distribution of double bonds in inner olefines can be controlled to some extent by adequately selecting the reaction temperature upon isomerization.

Next, the present invention is described in detail based on working examples and comparative examples, but the present invention is in no way limited to the following examples so long as the gist of the present invention is not exceeded.

EXAMPLE 1

Into a 10 lit. pressure resistant, sealed vessel equipped with a stirrer were charged 6 kg of 1-hexadecene (mfd. by Mitsubishi Chemical Industries Ltd., trade name DIAREN AO-16) and additionally 30g (0.5% by weight based on 1-olefine) of H-mordenite type zeolite (mfd. by TOYO SODA MFG. CO., LTD., trade name TSZ 650 XOA), and the inner space of the vessel was displaced by nitrogen gas. The reaction mixture was maintained at 150° C. for 4 hours by heating with stirring to effect isomerization reaction, then cooled to room temperature, and filtered with filter paper of 1 μm for separation of catalyst to thereby obtain inner olefines.

The double bond distribution of inner olefines obtained was determined by the ozone-triphenylphosphine reduction chromatography while the amount of self-polymer of 1-olefine as by-products was determined by high pressure liquid chromatopraphy.

The results are shown in Table 1.

EXAMPLE 2

Into a 1 lit. round-bottom flask were charged 500 g of mixed 1-olefines of 1-hexadecene and 1-octadecene (mfd. by Mitsubishi Chemical Industries Ltd., trade name DIAREN AO-168) and additionally 5 g (1.0% by weight based on 1-olefine) of Fe-mordenite type zeolite (mfd. by TOYO SODA MFG. CO., LTD., trade name TSZ-650 XOA, its hydrogen being exchanged with iron) as a catalyst. and the inner space of the round-bottom flask was displaced by nitrogen gas. The reaction mixture was maintained at 160° C. for 5 hours by heating with stirring to effect isomerization reaction, then cooled to room temperature, and filtered with filter paper of 1 μm for separation of catalyst to thereby obtain inner olefines.

The double bond distribution of inner olefines obtained was analyzed by $^{13}$C-NMR and the amount of self polymer of 1-olefines as by-products was determined by the same method as in Example 1.

The results are shown in Table 1.

EXAMPLE 3

Into a 10 lit. pressure resistant sealed vessel equipped with a stirrer were charged 6 kg of 1-eicosene (mfd. by Mitsubishi Chemical Industries Ltd., trade name DIAREN AO-20) and additionally 30g (0.5% by weight based on 1-olefine), and the inner space of the vessel was replaced by nitrogen gas. The reaction mixture was maintained at 200° C. for 4 hours by heating with stirring to effect isomerization reaction, and treated in the same manner as in Example 1 to obtain inner olefines.

Resulting inner olefines and self-polymer of 1-olefine were evaluated in the same manner as in Example 1.

The results are shown in Table 1.

EXAMPLE 4

Inner olefines were obtained by isomerization reaction under the same conditions followed by the same treatment as in Example 1 except that the amount of catalyst was changed to 3 g (0.05% by weight of 1-olefine).

Resulting inner olefines were evaluated in the same manner as in Example 1. The results are shown in Table 1.

COMPARATIVE EXAMPLE 1

Inner olefines were obtained by isomerization reaction under the same conditions followed by the same treatment as in Example 1 except that the reaction temperature was set at 90° C.

Resulting inner olefines were evaluated in the same manner as in Example 1. The results are shown in Table 1.

COMPARATIVE EXAMPLE 2

Inner olefines were obtained by isomerization reaction under the same conditions followed by the same treatment as in Example 1 except that the reaction temperature was set at 290° C.

Resulting inner olefines were eveluated in the same manner as in Example 1. The results are shown in Table 1.

COMPARATIVE EXAMPLE 3

Inner olefines were obtained by isomerization reaction under the same conditions followed by the same treatment as in Example 1 except that 0.5% by weight based on 1-olefine of silica/titania=10/1 was used instead of the catalyst in Example 1 and the reaction time was set at 9 hours.

Resulting inner olefines were eveluated in the same manner as in Example 1. The results are shown in Table 1.

COMPARATIVE EXAMPLE 4

Inner olefines were obtained by isomerization reaction under the same conditions followed by the same treatment as in Example 2 except that 1.0% by weight based on 1-olefines of silica/titania-10/1 was used instead of the catalyst in Example 2 and the reaction temperature and the reaction time were set at 170° C. and 9 hours, respectively.

Resulting inner olefines were evaluated in the same manner as in Example 2. The results are shown in Table 1.

COMPARATIVE EXAMPLE 5

Inner olefines were obtained by isomerization reaction under the same conditions followed by the same treatment as in Example 1 except that 1.0% by weight based on 1 olefine of silica/alumina/iron = 1/0.3/0.1 was used instead of the catalyst in Example 1 and the reaction time was set at 7 hours.

Resulting inner olefines were evaluated in the same manner as in Example 1. The results are shown in Table 1.

COMPARATIVE EXAMPLE 6

Inner olefines were obtained by isomerization reaction under the same conditions follwed by the same treatment as in Example 2 except that 1.0% by weight based on 1-olefines of silica/alunima/iron = 1/0.3/0.1 was used instead of the catalyst in Example 2 and the reaction temperature and the reaction time were set at 180° C. and 7 hours, respectively.

Resulting inner olefines were evaluated in the same manner as in Example 2. The results are shown in Table 1.

COMPARATIVE EXAMPLE 7

Inner olefines were obtained by isomerization reaction under the same conditions followed by the same treatment as in Example 2 except that 25 g (5.0% by weight based on 1-olefines) of 98% sulfuric acid was used instead of the catalyst in Example 2 and the reaction temperature was set at 200° C.

Resulting inner olefines were evaluated in the same manner as in Example 2. The results are shown in Table 1.

COMPARATIVE EXAMPLE 8

Inner olefines were obtained by isomerization reaction under the same conditions followed by the same treatment as in Example 2 except that 25 g (5.0% by weight based on 1-olefines) of potassium hydroxide was used instead of the catalyst in Example 2 and the reaction temperature was set at 200° C.

Resulting inner olefines were evaluated in the same manner as in Example 2. The results are shown in Table 1.

TABLE 1

| | number of carbons in 1-olefine | catalyst | catalyst amount (% by weight based on 1-olefine) | reaction temperature (°C.) | amount of formed polymer (% by weight) | composition of formed inner olefines (mol %) *1 | | | | |
|---|---|---|---|---|---|---|---|---|---|---|
| | | | | | | 1 | 2 | 3 | 4 | 5≦ |
| Example | | | | | | | | | | |
| 1 | 16 | H-mordenite type zeolite | 0.5 | 150 | 1.5 | 4 | 62 | 20 | 7 | 7 |
| 2 | 16-18 | Fe-mordenite type zeolite | 1.0 | 160 | 2.0 | 5 | 59 | 21 | 8 | 7 |
| 3 | 20 | H-mordenite type zeolite | 0.5 | 200 | 1.6 | 2 | 30 | 28 | 24 | 16 |
| 4 | 16 | H-mordenite type zeolite | 0.05 | 160 | 0.4 | 77 | 20 | 3 | 0 | 0 |
| Comparative Example | | | | | | | | | | |
| 1 | 16 | H-mordenite type zeolite | 0.5 | 90 | 0.6 | 65 | 30 | 5 | 0 | 0 |
| 2 | 16 | H-mordenite type zeolite | 0.5 | 290 | 5.3 | 2 | 28 | 27 | 20 | 23 |
| 3 | 16 | silica/titania = 10/1 | 0.5 | 150 | 6.5 | 10 | 42 | 28 | 14 | 6 |
| 4 | 16-18 | silica/titania = 10/1 | 1.0 | 170 | 8.0 | 15 | 43 | 21 | 15 | 6 |
| 5 | 16 | silica/alumina/iron = 1/0.3/0.1 | 1.0 | 150 | 7.5 | 8 | 39 | 28 | 14 | 11 |
| 6 | 16-18 | silica/alumina/iron = 1/0.3/0.1 | 1.0 | 180 | 9.6 | 12 | 38 | 25 | 9 | 16 |
| 7 | 16-18 | 98% H$_2$SO$_4$ | 5.0 | 200 | 18.0 | 24 | 20 | 18 | 17 | 21 |
| 8 | 16-18 | KOH | 5.0 | 200 | 0 | 100 | 0 | 0 | 0 | 0 |

Note *1 . . . The numberals designate the position of double bond in inner olefine.

We claim:

1. A process for preparing inner olefines comprising using 1-olefines having 6 to 34 carbon atoms as a starting material and conducting an isomerization reaction in the presence of an isomerization catalyst selected from the group consisting of mordenite and a zeolite having the same structure as mordenite at temperatures ranging from 130° to 180° C. and wherein 0.05 to 1.0 percent by weight of catalyst based on 1-olefine is present, and wherein the catalyst is present in the hydrogen form.

2. A process according to claim 1 wherein said isomerization reaction is conducted at temperature ranging from 150° to 180° C.

3. A process according to claim 1 wherein unreacted 1-olefines are separated and recirculated to be used as a starting material.

4. A process according to claim 1 wherein the 1-olefines are selected from the group consisting of linear 1-olefines or branched 1-olefines.

5. A process according to claim 1 wherein the catalyst is mordenite.